(12) United States Patent
Van Der Meer et al.

(10) Patent No.: US 6,661,467 B1
(45) Date of Patent: *Dec. 9, 2003

(54) SUBTITLING TRANSMISSION SYSTEM

(75) Inventors: Jan Van Der Meer, Eindhoven (NL);
Richard C. Spiero, Eindhoven (NL);
Armand V. Wemelsfelder, Hilversum
(NL); Wiebe De Haan, Eindhoven
(NL)

(73) Assignee: Koninklijke Philips Electronics N.V.,
Eindhoven (NL)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/572,255

(22) Filed: Dec. 13, 1995

(30) Foreign Application Priority Data

Dec. 14, 1994 (EP) .............................. 94203642

(51) Int. Cl.[7] .......................... H04N 5/445; G09G 5/02; G09G 5/00
(52) U.S. Cl. ........................ 348/564; 345/781; 345/601
(58) Field of Search ................. 348/468, 467, 348/465, 476, 589, 563, 564, 781, 601; 345/199; H04N 5/238

(56) References Cited

U.S. PATENT DOCUMENTS

| | | | | |
|---|---|---|---|---|
| 4,622,545 A | * | 11/1986 | Atkinson | 345/562 |
| 5,089,899 A | | 2/1992 | Nomura et al. | 358/335 |
| 5,091,717 A | * | 2/1992 | Carrie et al. | 345/806 |
| 5,101,365 A | * | 3/1992 | Westberg et al. | 345/807 |
| 5,424,785 A | * | 6/1995 | Orphan | 348/461 |
| 5,430,465 A | * | 7/1995 | Sabella et al. | 345/199 |
| 5,500,680 A | * | 3/1996 | Lee | 348/468 |
| 5,515,082 A | * | 5/1996 | Hirschaver et al. | 345/192 |
| 5,519,443 A | * | 5/1996 | Salomon et al. | 348/467 |
| 5,541,662 A | * | 7/1996 | Adams et al. | 348/460 |
| 5,559,999 A | * | 9/1996 | Maturi et al. | 348/7 |
| 5,579,057 A | * | 11/1996 | Banker et al. | 345/589 |
| 5,715,515 A | * | 2/1998 | Akins et al. | 725/142 |
| 5,742,352 A | * | 4/1998 | Tsukagoshi | 348/468 |

FOREIGN PATENT DOCUMENTS

| | | |
|---|---|---|
| EP | 0488676 | 6/1992 |
| JP | 646350 | 2/1994 |

* cited by examiner

*Primary Examiner*—Vivek Srivastava
(74) *Attorney, Agent, or Firm*—Laurie E. Gathman

(57) ABSTRACT

A method of simultaneously transmitting a video signal and encoded data representing graphic images is disclosed. The invention is particularly applicable for transmitting multi-lingual subtitles with a video program. The graphic images are rectangular regions within the active video area. They are transmitted in the form of bitmaps. The invention not only allows any character font or size to be displayed, but also the definition of e.g. a program provider's logo. The encoded data includes a time stamp to specify the time at which a subtitle is to be displayed. Preferred embodiments of the invention include the transmission of color-look-up-table (CLUT) data and a compatibility code indicating a required minimum number of entries of said color-look-up-table. For receivers with a CLUT having more entries than necessary, a map table is a for mapping the pixel data width to the input witdh of the relevant CLUT. The method is applicable to Direct Video Broadcast systems wherein the video signal is MPEG2 encoded and the graphic images are accommodated in a private data stream of an MPEG2 Transport Stream.

2 Claims, 4 Drawing Sheets

SUBTITLING TRANSMISSION SYSTEM

FIELD OF THE INVENTION

The invention relates to a method of transmitting encoded data defining a graphic image in the form of a rectangular region within an active video area. The invention also relates to a method of receiving said graphic images, and a transmitter and receiver arranged to carry out said methods.

BACKGROUND OF THE INVENTION

A prior art of transmitting graphic images is generally known by the name "teletext". The World System Teletext standard has been adopted in may countries for the simultaneous transmission of textual and graphic information with a conventional analog television signal. The teletext system is particularly used for the transmission of subtitles associated with a television program.

Meanwhile, the MPEG2 (ISO/IEC 13818) digital television standard will be applied worldwide for the broadcast of digital television program to the end-user by satellite, cable, terrestrial networks, and by packaged media such as tape or disc. A multitude of integrated circuits for MPEG2 decompression and demultiplexing are on the market and will be applied in receiver decoders for the purpose of receiving and decoding of broadcast television programs or decoding of packaged (multi-)media.

The MPEG2 compression and multiplexing technology will provide the end-user a very large choice in programs (typically in the order of hundreds), which will require an easy-to-use "man-machine interface". It is expected that the end-user will associate "digital" with high quality. High quality must therefore be manifest in all aspects of the service that will be provided. Typical of satellite broadcast is the large footprint of its reception area, which usually encompasses multiple language areas. Many of the television program to be broadcast will therefore also be targeted at multiple language areas, which requires multi-language subtitling capabilities. The attractiveness and readability of subtitles will have a major in one end-user's willingness to watch a television program in a language spoken other than his or her own.

The prior art teletext system is very limited in quality and performance. It is a character-based transmission system, in which coded data is transmitted to define which characters are to be displayed. The appearance of the subtitles (in terms of character font, spacing, graphic capabilities, colours) is fixed in hardware. Further, the present teletext system is not able to support complex character sets such as used in the People's Rpublic of China and Japan. The character-based system would require very expensive and complex character generators in case of supporting multiple character sets, or in case of a single but very complex character set. The prior art teletext system thus provides only a basic solution for multi-language subtitling.

OBJECT AND SUMMARY OF THE INVENTION

It is an object of the invention to overcome the above mentioned disadvantages of the prior art system. It is a further object to provide a universal solution for multilingual subtitling, in particular, for an MPEG2 environment.

The method according to the invention is characterized in that the pixels forming said region are individually defined by the encoded data, the size and position of said region being included in the encoded data. The method renders it possible for the program provides to control the appearance of the graphic images pixel-wise. The "Region based Graphic" system provides bitmapped rather than character coded regions overlaying the video signal. There are no restrictions as regards character size and character font, and there is a capability to overlay other graphics than text, e.g. the program provider's logo.

In an embodiment, the enclosed data further includes a time stamp representing the time at which said region is to be displayed. This allows multilingual subtitles to be transmitted in advance and to be displayed in exact synchronism with the video signal. In the prior art teletext system, the subtitles in the selected language are immediately displayed when received. More or less precise synchronization is possible only if all subtitles in the plurality of languages are transmitted within a restricted period of time.

Subsequent encoded data for a given region may include a visibility code to disable the display of said region. This allows for effectively erasing a graphic region.

In further embodiments of the invention, the pixels of a region are encoded as entries of a colour-look-up-table. Map tables are provided for mapping n-bit pixel codes to a colour-look-up-table having more than $2^n$ entries.

In an particularly advantageous embodiment, the encoded data is accommodated in a private transport stream according to the MPEG2 or a similar standard. Packetizing the encoded data in PES packets of an MPEG2 private transport stream has the advantage of easy synchronizing the bitmaps to an associated MPEG video system.

DESCRIPTION OF EMBODIMENTS

Figure 1:
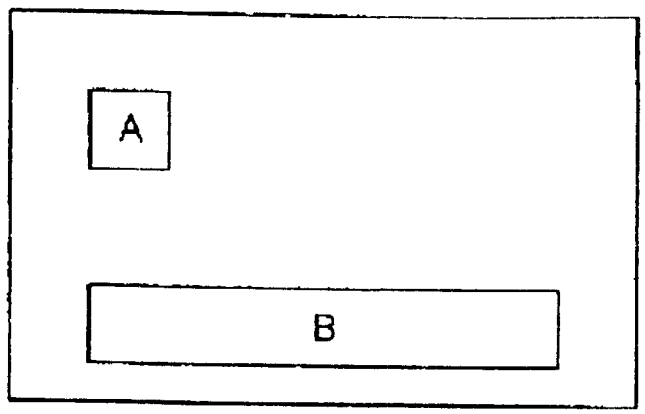
FIGS. 1–3 show examples of a display screen comprising one or more graphic image regions.

The invention will now first be described in terms of the transmission format. The syntax as described hereinafter is similar to the syntax used in the MPEG2 (ISO/IEC 13818) standard. The {and} symbols of this syntax have been omitted as they are not significant to the readability. Also omitted are data elements which are not essential to the invention or merely serve the purpose of byte alignment.

The encoded data defining the graphic images is packetized in PES (Packetized elementary Streams) packts and accommodated in an MPEG2 Transport Stream. As prescribed by the MPEG2 standard, the PES packets comprise a header and payload.

The header comprises a plurality of data elements, the following of which are relevant to the invention:

The element stream_id is set to "1011 1101" so as to indicate that the graphic image is conveyed as private_data_stream_1.

The element PES_packet_length is set to a value such that each PES packet is aligned with an MPEG2 transport packet.

The element data_alignment_indicator is set to '1', indicating that the region data fields an aligned with the PES packets.

The PTS (Presentation Time Stamp) indicates the beginning of the presentation time of each (region related) data contained in this PES packet. The PTSs of regions within one multi page shall differ more than 40 msec.

The payload of PES packet defining the graphic images is denoted PES_data_field( ). Table I shows the syntax of this field.

TABLE I

| PES_data_field() | | |
|---|---|---|
| data_identifier | 8 | uimsbf |
| RbG_stream_id | 18 | bslbf |
| stream_level_of_compatability | 3 | bslbf |
| single_page_display_flag | 1 | bslbf |
| for (i = O;N;i++) | | |
|   region_id | 8 | uimsbf |
|   region_level_of_compatability | 3 | bslbf |
|   region_data_length | 16 | uimsbf |
|   region_data_field() | | |

The following semantic definition applies to the data elements shown in this Table:

- data_identifier—Region based Graphics (RbG) data is identified by the values 0x20–0x2F of the data_identifier field.
- RbG_stream_id—Identifies the Region based Graphics stream from which data is stored in this PES packet.
- stream_level_of_compatibility—Indicates the minimum Colour-Look-Up-Table (CLUT) that is required to decode regions from this stream. The value 0x01 refers to a 2-bit CLUT, the value 0x02 refers to a 4-bit CLUT, and the value 0x03 refer to an 8-bit CLUT.
- single_page_display_flag—If set to '1', indicate, that this RbG stream contains only one display page.
- region_id—Identifies the region from which the data is contained in the immediately following region_data_field( ).
- region_level_of_compatibility—Indicates the minimum CLUT that is required to decode this region. The values defined above apply.
- region_data_length—Specifies the number of bytes in the immediately subsequent region_data_field( ) the syntax of which is given in Table II.

Table II shows the syntax of the region_data_field( ). The following semantic definition applies to the data elements shown in this Table:

- region_data_type—Identifies the type of region data. The value 0x10 refers to an intra region (I-region), the value 0x11 refers to region attributes (A-region), the value 0xFF indicates a region to be deleted.

TABLE II

| region_data_field() | | |
|---|---|---|
| region_data_field | 4 | bslbf |
| visibility_flag | 1 | bslbf |
| horizontal_address_flag | 1 | bslbf |
| vertical_address_flag | 1 | bslbf |
| number_of_pixels_flag | 1 | bslbf |
| number_of_lines_flag | 1 | bslbf |
| if (horizontal_address_flag = = '1') | | |
|   region_horizontal_address | 16 | uimsbf |
| if (vertical_address_flag = = '1') | | |
|   region_vertical_address | 16 | uimsbf |
| if (number_of_pixels_flag = = '1') | | |
|   number_of_pixels | 16 | uimsbf |
| if (number_of_lines_flag = = '1') | | |
|   number_of_lines | 16 | uimsbf |
| number_of_subregions | 4 | uimsbf |
| for (i=0;i<number_of_sub_regions;i++) | | |
|   sub_region_id | 4 | bslbf |
|   number_of_sub_region_lines_flag | 1 | bslbf |
|   clut_flag | 1 | bslbf |
|   attribute_extension_flag | 1 | bslbf |
|   coded_data_flag | 1 | bslbf |
|   coded_data_extension_flag | 1 | bslbf |
|   if (number_of_sub_region_lines_flag = = '1') | | |
|     number_of_sub_region_lines | 16 | uimsbf |
|   if (clut_flag = = '1') | | |
|     colour_look_up_table_data() | | |
|   if (attribute_extension_flag = = '1') | | |
|     attribute_extension_length | 8 | uimsbf |
|     for (i = 1;i<attribute_extension_length;i++) | | |
|       reserved | 8 | bslbg |
|   if (coded_data_flag = = '1') | | |
|     coded_sub_region_data() | | |
|   if (coded_data_extension_flag = = '1') | | |
|     coded_data_extension_length | 8 | uimsbf |
|     for (i = O;i<coded_data_extension_length;i++) | | |
|       reserved | 8 | bslbg |

- visibility_flag—If set to '1', specifies that this region shall be displayed as defined by th coded data for this region. If set to '0' this region shall be transparent.
- horizontal_address_flag—Indicates the presence of the region_horizontal_address field. In I-regions this flag shall be '1'.
- vertical_address_flag—Indicates the presence of the region_vertical_address field. In I-regions this flag shall be '1'.
- number_of_pixels_flag—Indicates the presence of the number_of_pixels field. In I-regions this flag shall be '1'.
- number_of_lines_flag—Indicates the presence of the number_of_lines field. In I-regions this flag shall be '1'.
- region_horizontal_address—Specifies the horizontal address of the top left pixel of this region. Within the frame of 720*576 pixels only even pixels shall be address. The most left pixel of the 720 active pixels has index zero, and the pixel address from left right. The horizontal address shall be such that each pixel of the region is within the active 720 pixels,
- region_vertical_address—Specifies the vertical address of the top line of this region. The top line of the 720*576 frame is line zero, and the line index increases by one within the frame from top to bottom. The vertical address shall be such that each line of the region is within the 576 active lines.
- number_of_pixels—Specifies the number of horizontal pixels of this region. A value of zero is forbidden.
- number_of_lines—Specifies the number of vertical lines of this region. A value of zero is forbidden.
- number_of_sub_regions—Specifies the number of sub-regions within this region. A value of zero is forbidden.
- sub_region_id—Identifies the sub-region.
- number_of_sub_region_lines_fag—Indicates the presence of the number_of_sub_region_lines field.
- clut_flag—Indicates the presence of the colour_look_up_data_field( ) field, the syntax of which is given in Table III.

attribute_extension_flag—If set to '1', indicates the presence of the attribute_extension_length field and the associated reserved fields.

coded_data_flag—Indicates the presence of the coded_sub_region_data( ) field which is defined in Table IV.

coded_data_extension_flag—If set to '1', identifies the presence of the coded_data_extension_length field and associated reserved fields.

number_of_sub_region_lines—Specifies the number of lines in a sub-region. The total number of lines in all sub-regions within the region shall be equal to the number of lines in the region.

attribute_extension_length—Specifies the number of immediately following reserved bytes.

coded_data_extension_length—Specifies the number of immediately following reserved bytes.

Table III shows the syntax of the colour_look_up_data field( ).

TABLE III

```
colour_look_up_table_data()
    number_of_entries                           9 uimsbf
    for (i=1;i<number_of_entries;i++)
        2_bit_clut_destination_flag             1 bslbf
        4_bit_clut_destination_flag             1 bslbf
        8_bit_clut_destination_flag             1 bslbf
        full_range_flag                         1 bslbf
        entry_value                             8 uimsbf
        if (full_range_flag = = '1')
            Y_value                             8 bslbf
            U_value                             8 bslbf
            V_value                             8 bslbf
            T_value                             8 bslbf
        else
            Y_value                             4 bslbf
            U_value                             4 bslbf
            V_value                             4 bslbf
            T_value                             4 bslbf
```

The following semantic definition applies to the data element shown in this Table:

number_of_clut_updates—Specifies the number of update cycles to be made.

number_of_entries—Specifies the number of CLUT entries that are updated.

2_bit_clut_destination_flag—If set to '1', indicates that this entry is intended for a 2-bit CLUT.

4_bit_clut_destination_flag—If set to '1', indicates that this entry is intended for a 4-bit CLUT.

8_bit_clut_destination_flag—If set to '1', indicates that this entry is intended for an 8-bit CLUT.

full_range_flag—If set to '1', indicates that the Y-value, U-value, V-value and T-value fields have full 8-bit resolution. If set to '0', then these fields contain only the 4 most significant bits.

entry_value—Specifies the entry value of the CLUT. The first entry of the CLUT has the entry value zero.

Y_value—The luminance output value of the CLUT for this entry.

U_value—The first chrominance output value of the CLUT for this entry.

V_value—The second chrominance output value of the CLUT for this entry.

T_vale—The transparency output value of the CLUT for this entry. A value of zero identifies no transparency. A value of 255 identifies full transparency. For all other values the level of transparency is defined by linear interpolation.

Table IV shows the syntax of the coded_sub_region_data( ).

The following semantic definition applies to the data elements shown in this Table:

data_block_length—Specifies the number of bytes of the coded_sub_region_data field immediately following this field.

coding_mode—Specifies the applied coding mode. If set to '00', identifying the presence of the mode_extension_field.

pixels_in_mode—Specifies the number of pixels coded by a 2, 4 or 8 bit code as specified by the coding_mode field.

2_bit_code—A two bit code specifying the colour of a pixel.

2_stuff_bits—two stuffing bits that shall be coded with '11'.

4_bit_code—A four bit code specifying the colour of a pixel.

4_stuff_bits—Four stuffing bits that shall be coded with '1111'.

8_bit_code—An eight bit code specifying the colour of a pixel.

mode_extension—Identifying the applied extension mode. If set to '00', identifies the presence of a command. If set to another value, identifies that run-length coding is applied.

10_bit_run—Specifying the number of subsequent pixels with the colour identified by the immediately following 2_bit_code field.

8_bit_run—Specifying the number of subsequent pixels with the colour identified by the immediately following 4_bit_code field.

4_bit_run—Specifying the number of subsequent pixels with the colour identified by the immediately following 8_bit_code field.

command_length—Specifying the number of bytes in this coded_sub_region_data( ) field immediately following the command_length field. If set to a value of 15, this number is not specified by the command_length field.

long_length—Specifies the number of bytes in this coded_sub_region_data( ) field immediately following the long_length field.

TABLE IV

```
coded_sub_region_data()
    data_block_length                                       16 uimsbf
    for (i=1;i<data_block_length;i++)
        coding_mode                                         2 bslbf
        if (coding_mode! = '00')
            pixels_in_mode                                  6 bslbf
            if (coding_mode = = '01')
                for (i=1;i<(pixels_in_mode+3)/4;i++)
                    for (i=1;i<pixels_in_mode;i++)
                        2_bit_code                          2 bslbf
                    for i + 1;i<(4*((pixels_in_mode+3)/4);
                         -pixels_in_mode;i++)
                        2_stuff_bits                        2 bslbf
            if (coding_mode = = '10')
                for (i=1;i<pixels_in_mode + 1)/2;i++)
                    for (i=1;i<pixels_in_mode;i++)
                        4_bit_code                          4 bslbf
                    for i = 1;i<(*((pixels_in_mode+1)/2-
                         pixels_in_mode;i++)
```

TABLE IV-continued

| | |
|---|---|
| 4_stuff_bits | 4 bslbf |
| if (coding_mode = = '11') | |
|   for (i=1;i<pixels_in_mode;i++) | |
|     8_bit_code | 8 bslbf |
| else | |
|   mode_extension | 2 bslbf |
|   if (mode_extension! = '00') | |
|     if (mode_extension= = '01') | |
|       10_bit_run | 10 uimsbf |
|       2_bit_code | 2 bslbf |
|     if (mode_extension= = '10') | |
|       8_bit_run | 8 uimsbf |
|       4_bit_code | 4 bslbf |
|     if (mode_extension= = '11') | |
|       4_bit_run | 4 uimsbf |
|       8_bit_code | 8 bslbf |
| else | |
|   command_length | |
|   if (command_length= = 15) | |
|     long_length | 16 uimsbf |
|   command_id | 8 bslbf |
|   if (command_id= =load_map_table) | |
|     map_table_data() | |
|   else | |
|     if (command_length! = 15) | |
|       for (i=1;i<command_length;i++) | |
|         reserved | 8 bslbf |
|     else | |
|       for (i=1;i<long_length;i++) | |
|         reserved | 8 bslbf | command_id—Identifies the type of command. The value 0x10 denotes Load Map Table. This command is followed by a map_table_data( ) field which is defined in Table V. The value 0x11 denotes End of Line.
Table V shows the syntax of the map_table_data( ).

TABLE V

| | |
|---|---|
| map_table_data() | |
|   number_of_entries | 8 uimsbf |
|   for (i = 1;i<number_of_entries;i++) | |
|     2_to_4_map_table_flag | 1 bslbf |
|     2_to_8_map_table_flag | 1 bslbf |
|     4_to_8_map_table_flag | 1 bslbf |
|     entry_value | 4 uimsbf |
|     map_table_output_value | 8 uimsbf |

The following semantic definition applies to the data element shown in this Table:

number_of_entries—Specifies the number of Map Table entries that are loaded.

2_to_4_map_table_flag—If set to '1', indicates that this entry is loaded into the "2 to 4 Map Table.

2_to_8_map_table_flag—If set to '1', indicates that this entry is loaded into the "2 to 8 Map Table.

4_to_8_map_table_flag—If set to '1', indicated that this entry is loaded into the "4 to 8 Map Table.

map_table_type—Identifies the type of Map Table that is loaded. The value '01' denotes a "2 to 4 Map Table", the value '10' denotes a "2 to 8 Map Table", the value '11' denotes a "4 to 8 Map Table".

entry_value—Specifies the entry of the Map Table. The first entry of the Map Table has the entry value zero.

map_table_output_value—Specifies the output value of the Map Table for this entry.

Figure 2:
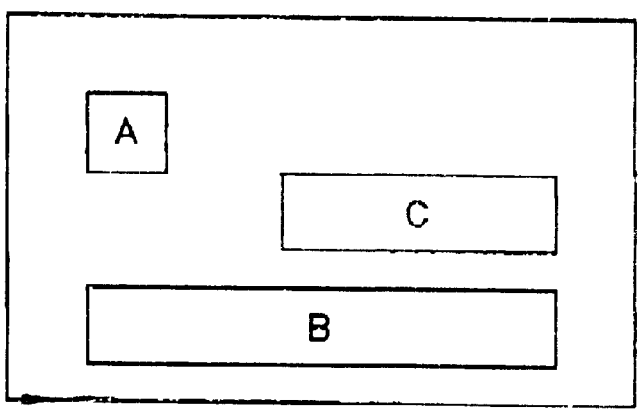
Figure 3:
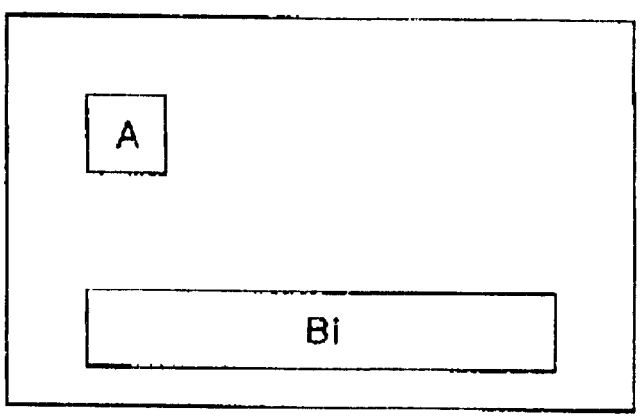

The above syntax and semantics will now be elucidated in a more common language. The PES_data_field( ) (Table I) specifies at least one "page" comprising one or more regions. FIGS. 1–3 show some examples of an active video area comprising one or more regions. FIG. 1 shows a program provider's logo A and a current subtitle B. FIG. 2 shows an additional subtitle C for hearing impaired viewers (hearing impaired people often need additional explanatory text such as "audience applauds", "swelling music"). FIG. 3 shows the logo A and a subtitle Bi, the index i indicating a selectable one from a plurality of languages.

Figure 4:
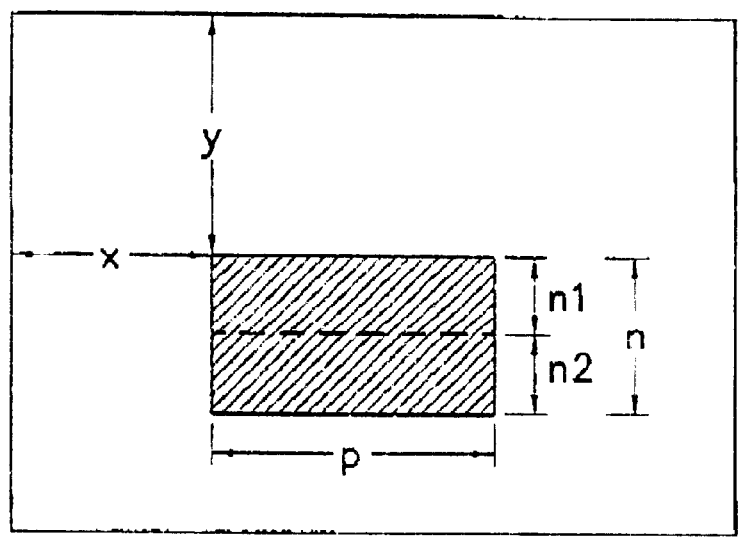
FIG. 4 shows a region with its relevant size and position parameters.

The data for each region is accommodated in the region_data_field( ) (Table II). This field specifies the size and position of the respective region. Referring to FIG. 4, the position of a region is (x,y), x being specified by region_horizontal_address and y by region_vertical_address. These position parameters can be changed in time which allows for scrolling, by retransmitting encoded data for a given region (specified by its region_id) without retransmitting pixel codes and colour-look-up-table data. The size of the region is p*n, p and n being specified by number_of_pixels and number_of_lines, respectively. Each region comprises up to 16 sub-regions. In FIG. 4, two subregions comprising $n_1$ and $n_2$ lines, respectively, are shown. The region_data_field( ) specifies colour-look-up-table data and/or pixel data for each subregion.

Not all parameters and data mentioned above are compulsory. Their presence is indicated by respective flags. This allows already defined regions and/or subregions to be updated or modified by referring to their region_id and/or sub_region_id, respectively. For example: the position of a region can be modified (which allows scrolling); an already displayed region can be made invisible; or a subregion can also be referred to by an other region and thus displayed elsewhere on screen without all image data being retrasmitted.

The colour-look-ut-table is loaded or updated by the colour_look_up_data( ) field (Table III). This field specifies which luminance, chrominance and transparency output values are to be stored in which entries of the CLUT. The transparency defines to what extent the video and graphics pixels are to be mixed on screen.

The pixel data for a subregion (or for a whole region is the number of subregions is I) is accommodated in the filed coded_sub_region_data( ) (Table IV). The pixels are defined as entries of the colour-look-up-table. The pixel values can be defined in 2, 4 or 8 bits. The coding modes are provided. In a first coding mode (coding_mode is '01', '10', '11'), consecutive pixels are individually specified. The number of pixels thus transmitted is defined by pixels_in_mode. In a second coding mode (coding_mode is '00', coding_mode_extension is '01', '10', '11'), runs of consecutive identical pixels are run-length encoded. The first and second coding modes can be mixed within a region. In order to minimise decoding complexity care has been taken that the run-length coded data is byte aligned. Each run-length code comprises two bytes; 2 bits for the coding mode, 2 bits for the coding mode extension and 12 bits for the run-length code. The latter defines a 10-bit run of 2-bit pixels, an 8-bit run of 4-bit pixels, or a 4-bit run of 8-bit pixels, as specified by the coding mode extension. A third coding mode (coding_mode is '00', coding_mode_extension is '00'), specifies commands such as map tables and end-of-line indicators which work on the run-length decoded data. The concept of map tables is disclosed in more details below.

It is envisaged that existing On-Screen-Display chips are used for displaying the graphic images. Some of these chips allow for 2 bits per pixel, others for 4 bits per pixel or 8 bits per pixel. A potential problem arises if the pixels within a region are encoded using a number of bits per pixel different from the colour-look-up-table's input width. In order to solve this problem, the concept of map tables has been introduced. Map tables also increase the coding efficiency. They allow pixels to be encoded in less bits per pixel than the entry-width of the colour-look-up-table. These aspects will now be elucidated by way of an example. Suppose a (sub)region in which only four different colours are used. The respective colours are stored, in terms of luminance and chrominance, in four entries of a CLUT. The pixel data for said region is encoded in 2 bits/pixel. The decoder, however, may have a 4-bit CLUT and thus require four bits per pixel. Now, the map table provides the mapping of the transmitted 2-bit/pixel codes to a 4-bit CLUT entry. The map table thus informs a decoder which four of the 16 entries are to be used. Whether or not the 2-bit/pixel coding indeed improves the efficiency depends on overhead to change the coding mode or the map table. Thus, map tables are provided for mapping n-bit/pixel coding to an m-bit CLUT, n and m being different numbers. In view of this elucidation of the concept of map tables, the map_table_data( ) field (Table V) needs no further explanation. For each entry value of the map table, an output value is defined.

Figure 5:
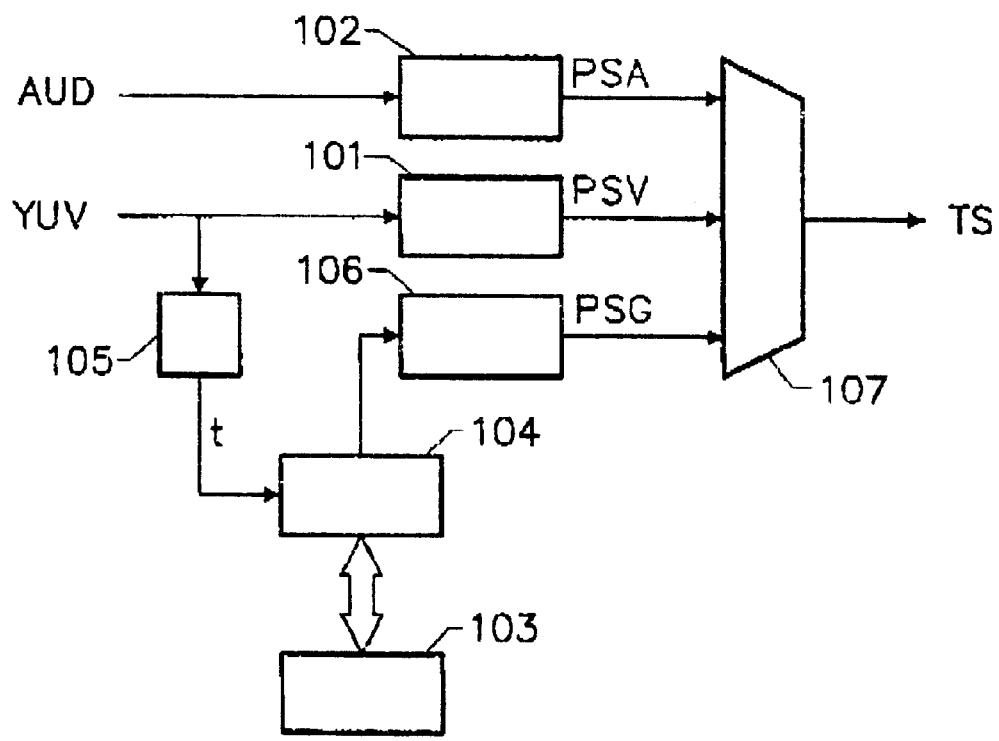
FIG. 5 shows a schematic diagram of a transmitter adapted to simultaneously transmit a video signal and graphic images according to the invention.

FIG. 5 shows a schematic diagram of a transmitter according to the invention. The transmitter is adapted to simultaneously transmit a video signal and graphic images The transmitter receives a baseband video signal in YUV format and an associated audio signal AUD and comprises a MPEG2 video encoder 101 and MPEG2 audio encoder 102 for encoding said video and audio signal into packetized elementary streams PSV and PSA, respectively. The transmitter comprises an editing 103 for editing subtitles and/or other graphic images such as a program provider's logo. The editing terminal is coupled to a processing and storage device 104. A plurality of subtitles associated with the relevant television program, possibly in a plurality of different languages, is assumed to be stored in the processing and storage device in advance. The video signal is also applied to a time generator 105 which applies a time t to the processor and storage device 104. The time t can be the time which has elapsed since the start of the relevant television program, or can be a time code associated with the program and stored on the same tape as the television signal. In MPEG systems, the t will correspond with MPEG's System Clock Reference SCR. The processor and storage device compares the time t with a time stamp associated with each stored subtitle. When a subtitle is due, the relevant data is applied to an encoding and packetized 106 which forms a packetized elementary stream PSG defining encoded data according to the transmission format discussed hereinbefore. The packetized elementary streams PSV, PSA and PSG are multiplexed by MPEG multiplexer 107 so as to form a transport stream TS. The transport stream is transmitted to a receiver via a transmission or storage medium (not shown).

Figure 6:
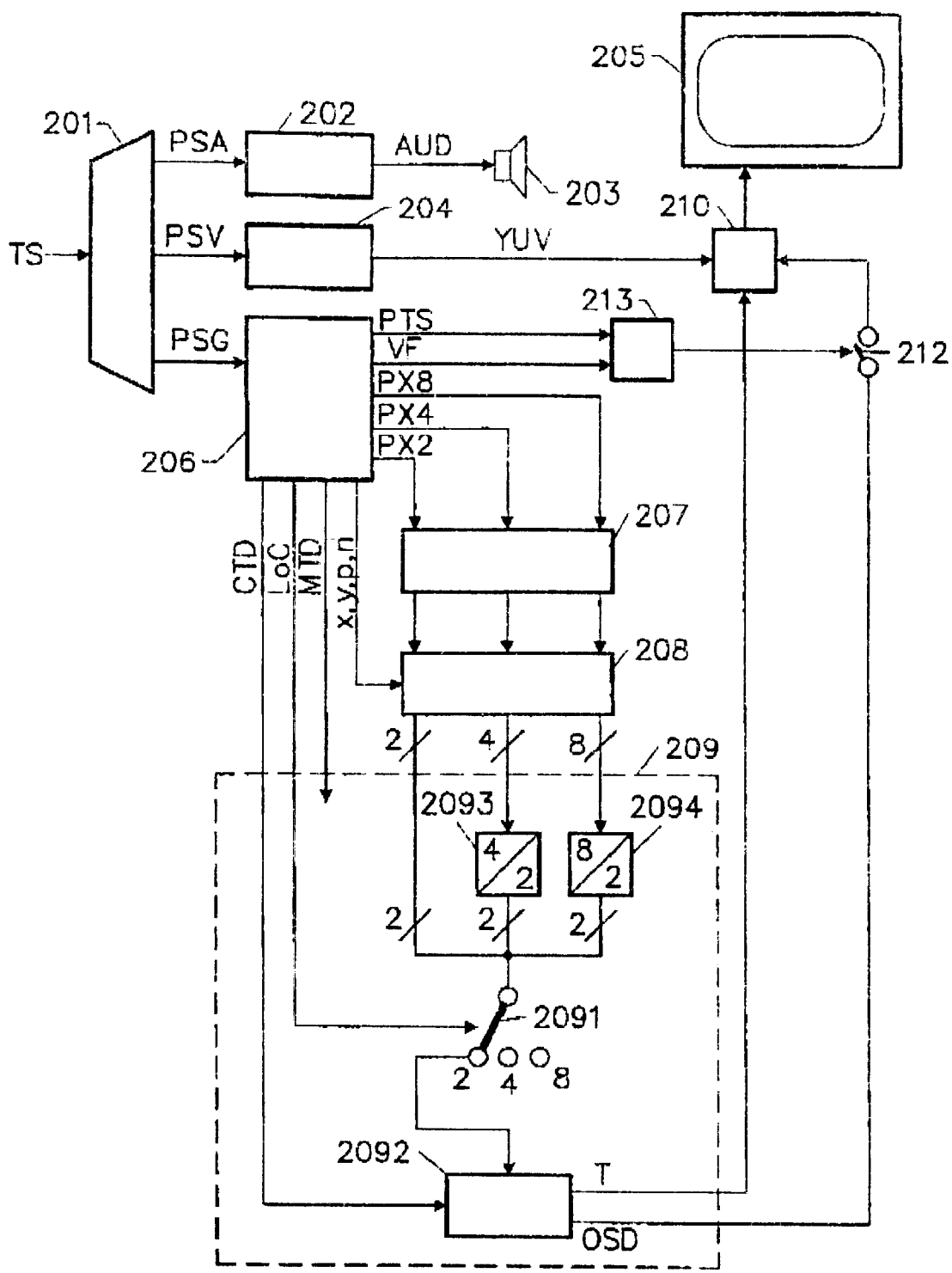
FIG. 6 shows a schematic diagram of a receiver for simultaneously receiving a video signal and graphic images according to the invention.

FIG. 6 shows a schematic diagram of a receiver according to the invention. The receiver comprises an MPEG2 demultiplexer 201 which receives the MPEG2 transport stream TS and selects the packetized audio stream PSA, video stream PSV and encoded graphics data PSG together constituting a selected television program. The audio stream is decoded by an MPEG2 audio decoder 202. The decoded audio signal AUD is applied to a speaker 203 for reproduction. The video stream is decoded by an MPEG2 video decoder 204 to obtain the decoded video signal in YUV format for display on a display screen 205. The encoded graphics data stream is applied to a data parser 206. This circuit parses the data accommodated in the PES packets PSG and provides the following output signals:

the presentation time stamp PTS accommodated in the PES header, indicating the time at which the region is to be displayed;

the value of the visibility_flag (Table II), denoted VF;

the encoded pixel data as defined by the fields n_bit_code in Table IV (n=2,4,8); 8-bit pixel codes are denoted PX8, 4-bit pixel codes are denoted PX4, and 2-bit pixel codes are denoted PX2;

the position (x,y) and size (p,n) of the currently received region as defined by the fields region_horizontal_address, region_vertical_address, number_of_pixels, and number_of_lines, respectively (Table II, FIG. 4);

map table data denoted MTD defined by the field map_table_data( ) (Table V), (this signal is not used in the present embodiment);

a signal denoted LoC derived from the field region_level_of_compatibility (Table I), and colour-look-up-table data denoted CTD, defined by the field colour_look_up_table_data( ) (Table III).

The pixel data PXn (n=2,4,8) received from the parser 206 is stored (when run-length encoded via a run-length decoder 207) in a pixel memory 208, the relevant memory locations being determined by position (x,y) and size (p,n) received from the parser. The pixel memory 208 is read out by display timing signals (not shown). The pixels PX2, PX4 or PX8 (a region may comprise both 2-, 4- and 8-bit pixels, but only one of them is active for the duration of a pixel) are thus applied to a colour generating circuit 209 in synchronism with the received video signal.

The colour generating circuit 209 comprises a colour-look-up-table 2092. In this embodiment, said CLUT is assumed to have four entries only, i.e. its input is 2 bits wide. The CLUT holds, for each entry, an output signal denoted OSD in terms of an 8-bit luminance value Y and 8-bit chrominance values U and V, and an 8-bit transparency value T. The relevant YUV and T values are stored in the CLUT in response to the colour-look-up-table data CTD received from the parser.

As the colour-look-up-table 2092 has a 2-bit input, the 2-bit pixels PX2 are directly applied thereto. The 4-bit pixels PX4 and 8-bit pixels PX8 are applied to the CLUT via a 4-to-2-bit reduction circuit 2093 and an 8-to-2-bit reduction circuit 2094, respectively. In a simple embodiment, said reduction circuits merely discard the least significant input bits. In an alternative embodiment, the most significant bit is unaltered (or some of the most significant bits are OR-ed) to obtain the first output bit whereas less significant input bits are OR-ed to obtain the second output bit.

The reduction circuits 2093 and 2094 allow higher level CLUT data (>2 bits) to be compatibly decoded by lower level CLUTs (2 input bits). However, a program provider may prevent regions defined by more than 4 colours to be decoded by 2-bit CLUTs. This is achieved by a switch 2091 controlled by the signal LoC received from the parser, i.e. by the field region_level_of_compatibility (see Table I). If the switch is in the position denoted 4 or 8 (i.e. the program provider requires at least a 4-bit CLUT or 8-bit CLUT, restively) the region will not be displayed. Only if the switch is in the position denoted 2 (i.e. the program provider accepts that pixels are displayed in four colours only), the pixel data is indeed applied to the CLUT.

In response to the 2-bit pixel codes, the CLUT 2092 delivers the display output signal OSD and the transparency signal T. The output signal OSD is applied to a mixing stage 210 in which it is mixed, on a pixel-by-pixel basis, with the video signal YUV. The transparency signal T determines the amount of transparency of graphic pixels. If T has the value 0, the video signal is blanked completely and the graphic pixels are not affected. If T has the value 255 (i.e. 100%), the relevant graphic pixel is fully transparent. For other values of T, the level of transparency is linearly interpolated. This allows the video signal to remain visible through the graphic image.

The combined signal is then displayed on the display screen 205. However, whether or not the graphic image is indeed displayed depends on a switch 212 which is controlled by a display enable circuit 213. This circuit receives the presentation time stamp PTS and the visibility flag VF from the parser, as well as (not shown) the current time t as conveyed by MPEG's System Clock Reference. The display enable circuit 213 is adapted to enable the display of the graphics region as soon as t>PTS and to disable its display when the visibility_flag for the relevant region is set to '0'.

Figure 7:
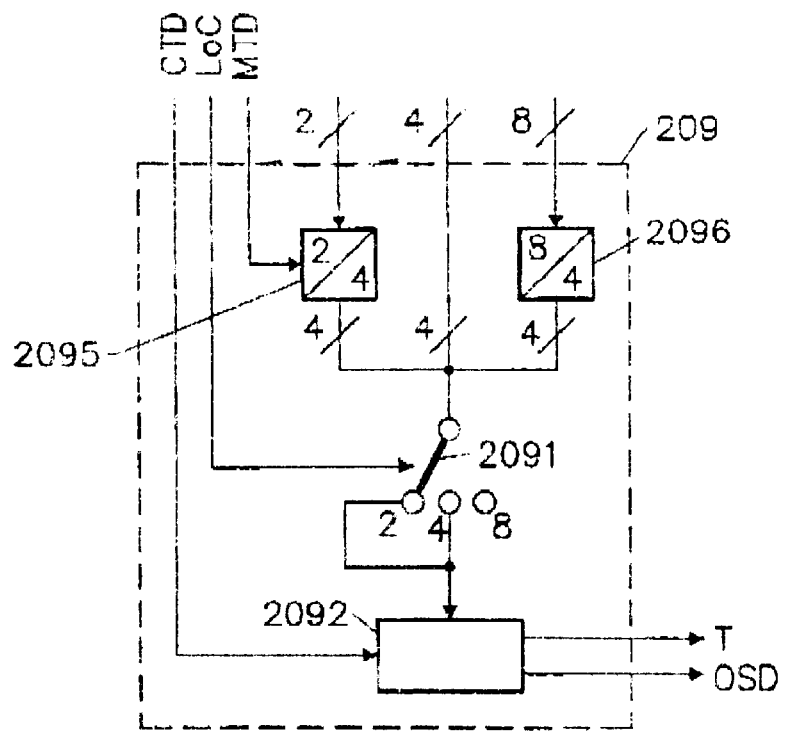
FIGS. 7 and 8 show embodiments of a colour generating circuit of the receiver shown in FIG. 6.

FIG. 7 shows a further embodiment of the colour generating circuit 209 of the receiver. In this embodiment, the CLUT 2092 of the receiver has a 4-bit input, i.e. the CLUT comprises sixteen entries. Now, the 4-bit pixels PX4 arc directly applied to the switch 2091 whereas the 8-bit pixels PX8 pass through an 8-to-4-bit reduction circuit 2096 which, for example, discards the four least significant input bits. The 2-bit pixels pass through a 2-to-4-bit map table 2095, in fact being a memory having four 4-bit locations. The map table 2095 maps the 2-bit pixels into 4-bit CLUT entries as specified by map table data MTD received from the parser. The concept of map tables has already been described before. If the switch 2091 is in the position denoted 8 (i.e. the program provider requires at least an 8-bit CLUT). the region will not be displayed. If the switch is in the position denoted 2 or 4 (i.e. the program provider accepts that 8-bit pixels are displayed in sixteen colours only), the pixel data is indeed applied to the CLUT.

Figure 8:
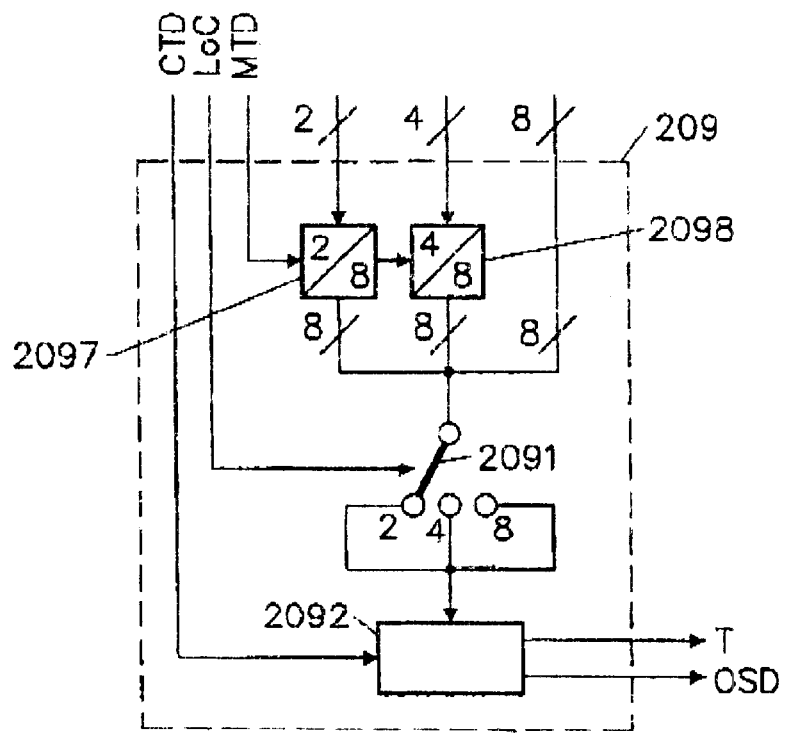

FIG. 8 shows an embodiment of the colour generating circuit 209 in which the CLUT 2092 has an 8-bit input, i.e. the CLUT comprises 256 entries. Now, the 8-bit pixels PX8 are directly applied to the switch 2091 whereas the 2-bit pixels PX2 and 4-bit pixels PX4 pass through a 2-to-8-bit map table 2097 and 4-to-8-bit map table 2098, respectively. The map table 2097 maps 2-bit pixels into 8-bit CLUT entries as specified by map table data MTD received from the parser. The map table 2098 does the same for 4-bit pixels. Strictly speaking, the switch 2091 is redundant in this embodiment, as this receiver deals with all transmissions regardless of the transmitted CLUT requirements.

As explained above, reduction circuits (2093, 2094, 2096) allow higher level CLUT data to be compatibly decoded by lower level CLUTs, whereas map tables (2095, 2097, 2098) allow lower level CLUTs to be dynamically mapped in higher level CLUTs. Table VI summarizes the various options and indicates the various levels of performance.

TABLE VI

| 2-bit CLUT | 0 | 0 | – | 0 | – | – |
|---|---|---|---|---|---|---|
| 4-bit CLUT | 0 | + | ++ | + | ++ | – |
| 8-bit CLUT | 0 | + | ++ | ++ | +++ | ++++ |
| | LoC = 2 | LoC = 2 | LoC = 4 | LOC = 2 | LoC = 4 | LOC = 8 |
| | 2-bit data | 4-bit data | | 8-bit data | | |

Table VI shows three rows indicating the performance of receivers having a 2-bit, 4-bit and 8-bit CLUT, respectively. Three columns indicate whether a region comprises 2-bit, 4-bit or 8-bit pixels, respectively. LoC denotes the level of compatibility included in the encoded data.

If a region is defined in 2 bits/pixel only, four colours can be displayed (performance denoted 0) irrespective of whether the CLUT input is 2, 4 or 8 bits wide. It does not make sense for a program provider to require, for such a region, a better than 2-bit CLUT. This is indicated by LoC=2 in the respective column.

If a region comprises 4-bit pixels, the program provider may allow such a region to be displayed using a 2-bit CLUT (LoC=2). Said 2-bit receivers display the region in four colours (performance denoted 0), whereas 4-bit and 8-bit receivers display 16 colours (performance denoted +). However, the program provider may also require the receiver to have a 4-bit CLUT (LoC=4). In that case, a 2-bit receiver can not display the region (performance denoted –) whereas 4-bit and 8-bit receivers will display 16 colours (performance denoted ++).

If a region comprises 8-bit pixels, the program provider may allow such a region to be displayed using a 2-bit CLUT (LoC=2). In that case, 2-bit receivers display 4 colours (performance denoted 0), 4-bit receivers display 16 colours (performance denoted +), and 8-bit receivers display the full pallet of colours (performance denoted ++). The program provider may also require the receiver to have at least a 4-bit CLUT (LoC=4). In that case, 2-bit receivers can not display the relevant region (performance denoted –), 4-bit receivers display 16 colours (performance denoted ++), and 8-bit receivers display the full pallet of colours (performance denoted +++). If the program provider requires receiver to have an 8-bit CLUT (LoC=8), neither 2-bit nor 4-bit receivers can display the relevant region (performance denoted –), whereas 8-bit receivers have an optimal performance (denoted ++++). The latter performance is optimal because the program provider does not need to the restrictions of lower level receivers into account.

Summarizing the invention, a method of simultaneously transmitting a video signal and encoded data representing graphic images is disclosed. The invention is particularly applicable for transmitting multilingual subtitles with a video program. The graphic images rectangular regions within the active video areas. They are transmitted in the from of bitmaps. The invention not only allows any character font or size to be displayed, but also the definition of e.g. a program provider's logo. The encoded data includes a time stamp to specify the time at which a subtitle is to be displayed. Preferred embodiments of the invention include the transmission of colour-look-up-table (CLUT) data and a compatibility code indicating a required minimum number of entries of said colour-look-up-table. For receivers with a CLUT having more entries than necessary, a map table is transmitted for mapping the pixel data width to the input witdh of the relevant CLUT. The method is applicable to Direct Video Broadcast systems wherein the video signal is MPEG2 encoded and the graphic images are accommodated in a private data stream of an MPEG2 Transport Stream.

What is claimed is:

1. A transmission device comprising:
   an encoder for encoding individual pixels for forming a graphic image on a display; and
   a transmitter for transmitting encoded data defining said graphic image in a rectangular region within an active video area on a display, wherein said encoded data further includes the size and position of said rectangular region and a time stamp representing the time at which said region is to be displayed and wherein the pixels for said rectangular region are encoded as entries of a colour-look-up-table and the encoded data further includes a compatibility code indicating a required minimum number of entries of said colour-look-up-table.

2. A receiver coupled to a display screen comprising:

a decoder for decoding encoded data into individual pixels defining a graphic image in the form of a rectangular region within an active video area on a display, said decoder further decoding said encoded data into individual pixels constituting said rectangular region wherein said encoded data further including the size and position of said region and a time stamp and wherein the pixels for said rectangular region are encoded as entries of a colour-look-up-table and the encoded data further includes a compatibility code indicating a required minimum number of entries of said colour-look-up-table; and a video display for storing and displaying said pixels with said size and position at a time represented by said time stamp.

* * * * *